(12) United States Patent
Phillion

(10) Patent No.: US 6,297,271 B1
(45) Date of Patent: Oct. 2, 2001

(54) OXIME AMIDES AND HYDRAZONE AMIDES HAVING FUNGICIDAL ACTIVITY

(75) Inventor: Dennis P. Phillion, St. Charles, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 09/636,345

(22) Filed: Aug. 10, 2000

Related U.S. Application Data

(60) Provisional application No. 60/149,017, filed on Aug. 13, 1999.

(51) Int. Cl.[7] .................... A61K 31/381; C07D 333/22
(52) U.S. Cl. .................................. 514/438; 549/76
(58) Field of Search .................... 549/76; 514/438

(56) References Cited

U.S. PATENT DOCUMENTS

| | | | |
|---|---|---|---|
| 4,228,165 | 10/1980 | Ogata et al. | 424/248.5 |
| 4,248,869 | 2/1981 | Ogata et al. | 424/248.5 |
| 4,999,381 | 3/1991 | Crowley et al. | 514/618 |
| 5,053,073 | 10/1991 | Anthony et al. | 71/94 |
| 5,482,974 | 1/1996 | Phillion et al. | 514/619 |
| 5,486,621 | 1/1996 | Phillion et al. | 549/4 |
| 5,693,667 | 12/1997 | Phillion et al. | 514/461 |
| 5,705,513 | 1/1998 | Phillion | 514/354 |

FOREIGN PATENT DOCUMENTS

| | | |
|---|---|---|
| 0 538 231 A1 | 4/1993 | (EP). |
| 63 284 186 | 11/1988 | (JP). |
| WO 93 07116 A | 4/1993 | (WO). |
| WO 9524380 | 9/1995 | (WO). |
| WO 96 23763 | 8/1996 | (WO). |

OTHER PUBLICATIONS

White, et al, Pesticide Biochemistry and Physiol, 25:188–204, 1986.
International Search Report, PCT International Searching Authority, Nov. 15, 2000.

Primary Examiner—Jane C. Osweckı
Assistant Examiner—Golam M. M. Shameem
(74) Attorney, Agent, or Firm—Thomas P. McBride; Howrey Simon Arnold & White, LLP

(57) ABSTRACT

The invention relates to compounds having usefulness in the control of Take-All disease in plants, particularly cereals, a method for the control of Take-All disease, and fungicidal compositions for carrying out the method. Compounds of the invention are oximes or hydrazones of arylgloxamides or heteroarylglyoxamides or cycloalkenylglyoxamides.

9 Claims, No Drawings

OXIME AMIDES AND HYDRAZONE AMIDES HAVING FUNGICIDAL ACTIVITY

This application is a conversion of provisional application serial no. 60/149,017 filed Aug. 13, 1999, the entitled contents of which are incorporated herein by reference.

FIELD OF THE INVENTION

The present invention relates to compounds useful in the control of Take-All disease in plants, particularly cereals, a method for the control of Take-All disease, fungicidal compositions for carrying out the method, and processes for the preparation of the compounds of the present invention.

BACKGROUND OF THE INVENTION

Take-All disease is a serious problem in the production of cereals, particularly wheat and barley. It is caused by the soil-borne fungus *Gaeumannomyces graminis* var. tritici (Ggt). The fungus infects the roots of the plant, and grows throughout the root tissue, causing a black rot. The growth of the fungus in the roots and lower stem prevents the plant from obtaining sufficient water and/or nutrients from the soil, and is manifested as poor plant vigor and, in severe instances of disease, the formation of "whiteheads," which are barren or contain few, shriveled grains. Yield losses result. *Gaeumannomyces graminis* species also infect other cereal crops, for example, rice and oats, and turf.

Currently the primary means of avoiding crop loss due to infestation of the soil by Ggt has been to rotate the crop grown to one which is resistant to Ggt. In areas where the primary crops are cereals, however, rotation is not a desirable practice, and an effective control agent is greatly desired.

It is an object of this invention to provide an effective method for control of Take-All disease in plants. It is a further object of this invention to provide compounds that control the growth of Ggt in the soil so as to reduce crop loss. It is a still further object of this invention to provide fungicidal compositions that may be used for control of Take-All disease.

Control of Take-All disease has been the subject of a number of commonly assigned patents, including U.S. Pat. Nos. 5,482,974, 5,486,621, 5,693,667 and 5,705,513. Published foreign applications include EP 0538231 A1 and WO 95/24380.

This invention includes a new family of chemical compounds found effective for control of Take-All disease which are different from those disclosed in the previous patents and published applications, as will be seen in the description and Examples below.

International Publication No. WO 96/23763 is assigned to Bayer AG and relates to alkoximino acetic acid amides for use as fungicides. In some respects, the compounds are similar to those of the present invention. They differ in requiring ring compounds in the amide group, and in the preferred oxime geometry. More importantly, of the many fungal species mentioned in the application, there is no reference to the fungus responsible for Take-All disease, Ggt.

SUMMARY OF THE INVENTION

In one aspect, the present invention is a family of chemical compounds having the following structural formula:

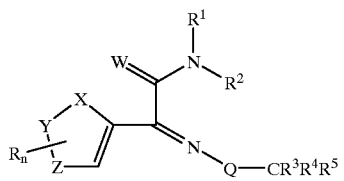

where
X and Y are each CH when Z is CH=CH, O, or S; or
X is O or S when Y and Z are CH; or
X is $CH_2$ or $CH_2CH_2$ when Y and Z are each $CH_2$;
W is O or S;
Q is O, NH, or NMe;
n=0–2;
R is independently selected from halo or alkyl;
$R^1$ is selected from the group consisting of $C_1$–$C_{10}$ straight or branched alkyl, alkenyl, or alkynyl groups, each optionally substituted with one or more halogen, alkoxy, alkylthio; alkoxy, alkenoxy, alkynoxy, dialkylamino, or alkylthio;
$R^2$ is selected from the group consisting of hydrogen; $C_1$–$C_6$ straight or branched alkyl, alkenyl, or alkynyl groups, each optionally substituted with one or more halogen;
$R^3$, $R^4$ and $R^5$ are independently selected from the group consisting of alkyl, alkenyl, alkynyl, cycloalkyl, cycloalkenyl, and phenyl, each optionally substituted with halogen, alkoxy, or alkylthio;
any two of said $R^3$, $R^4$ and $R^5$ groups optionally combined to form a cyclo group which is cyclopropyl, cyclobutyl, cyclopentyl, or cyclohexyl.

In another aspect, the invention is a new method of controlling Take-All disease by applying an effective amount of compounds defined above to the plant locus, preferably along with an adjuvant. It has been found that the effectiveness of the new compounds is often affected by their isomeric form. In general, Z geometric isomers are preferred over E geometric isomers.

Compounds of the invention may be classified as oximes or hydrazones of arylgloxamides or heteroarylglyoxamides or cycloalkenylglyoxamides, depending on the definitions of Q, X, Y, and Z in the general formula.

DESCRIPTION OF ILLUSTRATIVE EMBODIMENTS

Definitions

As used herein, the term "alkyl," unless otherwise indicated, means an alkyl radical, with a straight or branched chain, having from 1–10 carbon atoms, with 1–6 carbon atoms being preferred. The terms "alkenyl" and "alkynyl" mean unsaturated radicals having from 2–7 carbon atoms, with 2–4 carbon atoms being preferred. Examples of such alkenyl groups include ethenyl, 1-methylethenyl, 1-propenyl, 2-propenyl, 1-butenyl, 2-butenyl, 3-butenyl, 2-methyl-1-propenyl, and 2-methyl-2-propenyl. Examples of such alkynyl groups include ethynyl, 1-propynyl, 2-propynyl, and 1,1-dimethyl-2-propynyl. Substituent groups may also be both alkenyl and alkynyl, for example, 6,6-dimethyl-2-hepten-4-ynyl.

As used herein, the term "alkoxy" means an alkyl group having, unless otherwise indicated, from 1–10 carbon atoms connected via an ether linkage. Examples of such alkoxy groups include methoxy, ethoxy, propoxy, 1-methylethoxy, and so forth.

As used herein, the term "halo" means a radical selected from chloro, bromo, fluoro, and iodo.

Compounds

The chemical compounds of the invention are generally called oximes, hydrazones of arylgloxamides, heteroarylglyoxamides, or cycloalkenylglyoxamides. They are defined by the following formula:

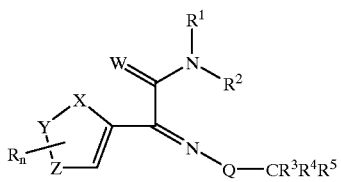

where X, Y, Z, W, Q, n, R, $R^1$, $R^2$, $R^3$, $R^4$ and $R^5$ are defined above.

The compounds include oxime or hydrazone substituents and amide or thioamide substituents, both attached to a ring compound, which may be a phenyl, thienyl, furyl, 1-cyclopentenyl, or 1-cyclohexenyl ring.

As will be seen in the Examples below, the isomers exhibit different biological activity. It has been found that geometric isomers with $C(W)NR^1R^2$ and $QC(R^3)_3$ in a cis-relationship have better activity for control of Take-All Disease than do the corresponding trans-geometric isomers.

Preferred compounds are those in which the ring is phenyl and

W is O

Q is O $R^1$ is propyl or allyl $R^2$ is hydrogen $R^3$, $R^4$ and $R^5$ are methyl or ethyl.

Processes For Making Compounds

Two general methods for preparing these compounds differ primarily in the order that their synthesis steps are carried out. In the most versatile route, shown below, esters of phenylglyoxylic acid can be prepared through reaction of phenylglyoxylyl chloride with alcohols in the presence of a suitable amine base. These esters are reacted with a salt of an O-(tert-alkyl)hydroxylamine (X=O) or an N-(tert-alkyl)hydrazine (X=NH or NMe) in the presence of a suitable amine base and solvent at reflux temperature to form the corresponding oxime or hydrazone. Suitable amine bases include triethylamine, diisopropylethylamine, and pyridine. Alternatively, the free base of the O-substituted oxime or N-substituted hydrazine can be used in a suitable solvent to directly form the oxime and hydrazone derivatives without an added amine base. Suitable solvents for the above reactions include alcohols such as methanol or ethanol.

For O-(tert-alkyl)hydroxylamines with tert-alkyl groups larger than tert-butyl, such as where R" is hydrogen or methyl, oxime formation can be mediated by running the reaction in hexane with an equivalent of $TiCl_4$.

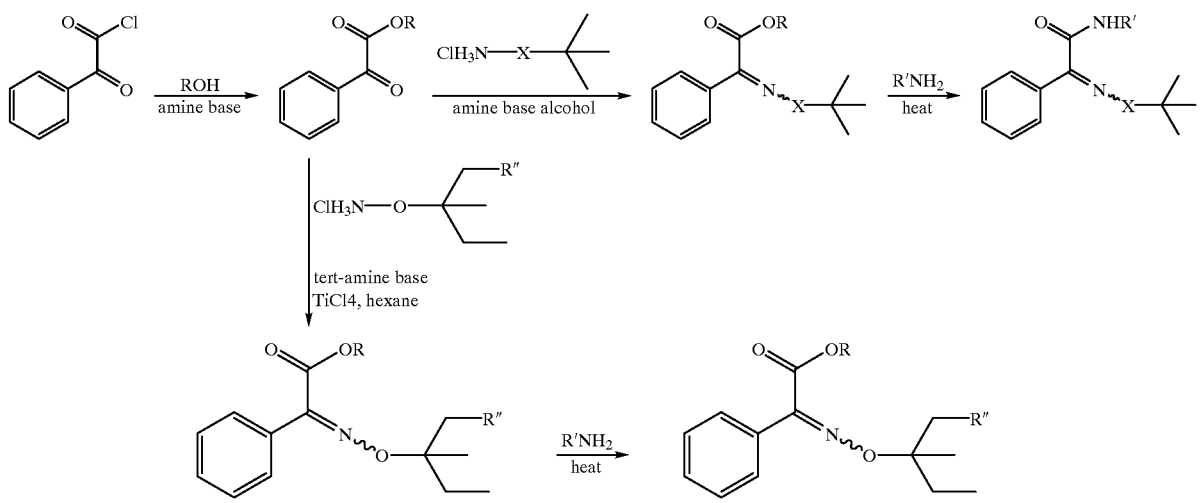

An E/Z mixture of oximes or hydrazones forms under all of these conditions with the Z isomer usually predominant for the O-(tert-butyl)oximes and N-(tert-butyl)hydrazones, and the E isomer usually predominant for larger O-(tert-alkyl)oximes and N-(tert-alkyl)hydrazones. For small esters of phenylglyoxylate, such as methyl, both O-(tert-alkyl)oximes and N-(tert-butyl)hydrazones can be readily separated by chromatography. Each of the O-(tert-alkyl)oxime geometric isomers can be reacted with a primary amine as solvent in a sealed tube at 100–150° C. to afford excellent yields of the corresponding amide without isomerization of the oxime geometry.

General methods for synthesizing esters of substituted glyoxylates employ the conversion of aryl, heteroaryl, or cycloalkenyl acid chlorides to their corresponding acyl nitriles. These conversions are mediated by reaction with CuCN in refluxing acetonitrile, or by reaction with TMSCN catalyzed by tin chloride at 0° C. Standard methods which convert these acyl nitriles directly to their aryl, cycloalkenyl, and heteroarylglyoxylate esters include hydrolysis in a mixture of 85% $H_2SO_4$, $Ac_2O$, and NaBr, followed by esterification in refluxing methanol. These methyl esters of substituted glyoxylic acids also undergo oxime and hydrazone formation as described above.

In an alternate route, shown below, the amide is first formed from reaction of phenylglyoxylyl chloride with a primary or secondary amine. This transformation can be carried out either by addition of the acid chloride to a solution of the primary or secondary amine and a suitable trialkylamine base in a suitable aprotic solvent, or by addition of the acid chloride to a vigorously stirred mixture of a solution of the primary or secondary amine in an aprotic solvent and a solution of a carbonate base in water. Suitable aprotic solvents for these transformation include methylene chloride, chloroform, diethylether, and ethyl acetate.

The amides are then reacted with a salt of an O-(tert-alkyl)hydroxylamine (X=O) or an N-(tert-alkyl)hydrazine (X=NH or NMe) in the presence of a suitable amine base and alcohol at reflux temperature to form the corresponding oxime or hydrazone. Suitable amine bases include triethylamine, diisopropylethylamine, and pyridine. Alternatively, the free base of the O-substituted oxime or N-substituted hydrazine can be used in a suitable alcohol solvent to directly form the oxime and hydrazone derivatives without added amine base. Suitable alcohol solvents can be methanol or ethanol.

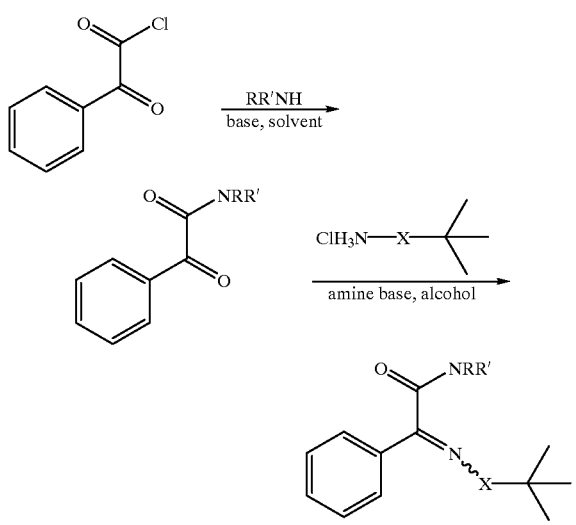

Control Of Take-All Disease

Control of Take-All diseases using a chemical control agent may be accomplished in several ways. The agent may be applied directly to soil infested with Ggt, for example, at the time of planting along with the seed. Alternatively, it may be applied after planting and germination. Preferably, however, it is applied to the seed in a coating prior to planting. This technique is commonly used in many crops to provide fungicides for control of various phytopathogenic fungi.

Compositions of the present invention are comprised of a fungicidally effective amount of one or more of the compounds described above and one or more adjuvants. The active ingredient may be present in such compositions at levels from 0.01–95 wt. %. Other fungicides may also be included to provide a broader spectrum of fungal control. The choice of fungicides will depend on the crop and the diseases known to be a threat to that crop in the location of interest.

The fungicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely divided particulate solids, granules, pellets, solutions, dispersions, or emulsions. Thus, it is believed that the active ingredient could be used with an adjuvant, such as a finely divided solid, a liquid of organic origin, water, a wetting agent, a dispersing agent, an emulsifying agent, or any suitable combination of these.

Suitable wetting agents are believed to include alkyl benzene and alkyl naphthalene sulfonates, sulfated fatty alcohols, amine of acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol), and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate. Stabilizers may also be used to produce stable emulsions, such as magnesium aluminum silicate, and xanthan gum.

Other formulations include dust concentrates comprising from 0.1–60 wt. % of the active ingredient on a suitable extender, optionally including other adjuvants to improve handling properties, e.g., graphite. These dusts may be diluted for application at concentrations within the range of from about 0.1–10 wt. %.

Concentrates may also be aqueous emulsions prepared by stirring a nonaqueous solution of a water-insoluble active ingredient and an emulsification agent with water until uniform, and then homogenizing to give stable emulsion of very finely divided particles. Or, they may be aqueous suspensions prepared by milling a mixture of a water-insoluble active ingredient and wetting agents to give a suspension, characterized by its extremely small particle size, so that when diluted, coverage is very uniform. Suitable concentrations of these formulations contain from about 0.1–60 wt. % (preferably 5–50 wt. %) of the active ingredient.

Concentrates may be solutions of the active ingredient in suitable solvents together with a surface active agent. Suitable solvents for the active ingredients of this invention for use in seed treatment include propylene glycol, furfuryl alcohol, other alcohols or glycols, and other solvents which do not substantially interfere with seed germination. If the active ingredient is to be applied to the solid, then solvents such as N,N-dimethylformamide, dimethylsulfoxide, N-methylpyrrolidone, hydrocarbons, and water-immiscible ethers, esters, or ketones may be used.

The concentrate compositions herein generally contain from about 1.0–95 parts (preferably 5–60 parts) active ingredient, about 0.25–50 parts (preferably 1–25 parts) surface active agent and, where required, about 4–94 parts solvent, all parts being by weight based on the total weight of the concentrate.

For application to the soil at the time of planting, a granular formulation may be used. Granules are physically stable particulate compositions comprising at least one active ingredient adhered to or distributed through a basic matrix of an inert, finely divided particulate extender. In order to aid leaching of the active ingredient from the particulate, a surface active agent such as those listed hereinbefore or, for example, propylene glycol, can be present in the composition. Natural clays, pyrophyllites, illite, and vermiculite are examples of operable classes of particulate mineral extenders. The preferred extenders are the porous, absorptive, preformed particles such as pre-formed and screened particulate attapulgite or heat expanded, particulate vermiculite, and the finely divided clays such as kaolin clays, hydrated attapulgite, or bentonitic clays. These extenders are sprayed or blended with the active ingredient to form the fungicidal granules.

The granular compositions of this invention may contain from about 0.1–30 parts by weight of active ingredient per 100 parts by weight of clay and 0 to about 5 parts by weight of surface active agent per 100 parts by weight of particulate clay.

The method of the present invention may be carried out by mixing the composition comprising the active ingredient into the seed prior to planting at rates from 0.01–50 g per kg of seed, preferably from 0.1–5 g per kg, and more preferably from 0.2–2 g per kg. If application to the soil is desired, the compounds may be applied at rates from 10–1000 g per hectare, preferably from 50–500 g per hectare. The higher application rates will be needed for situations of light soils, greater rainfall, or both.

Experimental Procedures

EXAMPLE 1

Synthesis Of Acylnitrile Intermediate A

A 1 M solution of tin chloride in $CH_2Cl_2$ (1.3 mL, 1.3 mmol) was added dropwise to an ice water cooled solution of p-toluoyl chloride (10.00 g, 65 mmol) and TMSCN (9.00 mL, 68 mmol). The reaction was monitored to completion over 4 hours by disappearance of the IR acid chloride carbonyl stretch, then quenched by addition of ice water (20 mL) and extracted with $CH_2Cl_2$. The organic solution was dried ($MgSO_4$) and concentrated to afford 8.80 g of p-toluoyl cyanide as an orange solid.

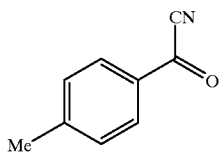

EXAMPLE 2

General Synthesis Of Acylcyanide Intermediates B & C

A mixture of a substituted benzoyl chloride (100 mmol) and CuCN (200 mmol) was refluxed in $CH_3CN$ (100 mL) and monitored to completion over 2 hours by disappearance of the IR acid chloride carbonyl stretch. The resulting reaction was filtered through a celite pad and concentrated to remove the acetonitrile, then diluted with toluene (100 mL) and filtered again. Concentration of the toluene filtrate and kugelrohr distillation afforded the following substituted benzoyl cyanides.

Intermediate B

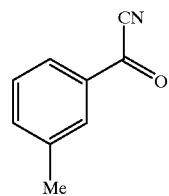

3-methylbenzoyl cyanide was isolated as a white solid in 52% yield. bp 55–60° C. at 0.2 Torr. Carbon NMR (76 MHz, $CDCl_3$) δ 21.1, 112.9, 127.9, 129.5, 130.7, 133.7, 137.7, 139.8, 168.

Intermediate C

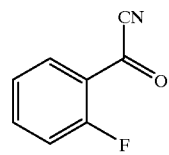

2-fluorobenzoyl cyanide was isolated as an oil in 46% yield. bp 50° C. at 1 Torr. Carbon NMR (76 MHz, $CDCl_3$) δ 113.2, 117.5, 117.8, 122.2, 125.1, 132.3, 138.5, 138.6, 161, 163.7, 164.5.

EXAMPLE 3

General Synthesis Of Arylglyoxylate Intermediates D–F

A solution of intermediate A, B, or C (60 mmol) in acetic anhydride (4 mL) was added to ice cold solution of aqueous 85% $H_2SO_4$·(100 mL). NaBr (6 mmol) was added and the mixture heated at 70° C. for 10 minutes with appearance of bromine. MeOH (60 mL) was then added and the reaction refluxed at 112.8° C. for 30 minutes. This was cooled to room temperature, diluted with ice water and extracted twice with ethyl acetate. The organic extracts were combined, dried ($MgSO_4$), concentrated, and purified by vacuum distillation to separate the mixture of desired methyl arylglyoxylate and corresponding substituted methylbenzoate. The following methyl arylglyoxylates were prepared.

Intermediate D

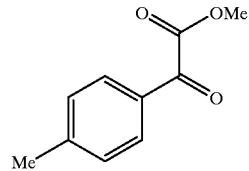

Methyl 4-methylphenylglyoxylate was isolated as an oil in 88% yield. Proton NMR (90 MHz, $CDCl_3$), δ 2.4 (s, 3H), 4.0 (s, 3H), 7.2–8.1 (AB, 4H).

Intermediate E

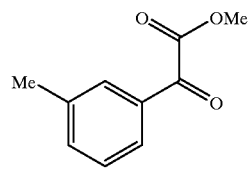

Methyl 3-methylphenylglyoxylate was isolated as an oil in 62% yield. Proton NMR (90 MHz, $CDCl_3$), δ 2.4 (s, 3H), 4.0, (s, 3H), 7.3–8.1 (m, 4H). Carbon NMR (76 MHz, CDCl₃) δ 20.9, 52.5, 127.1, 128.6, 130.0, 135.5, 136.7, 164.1, 186.1.

Intermediate F

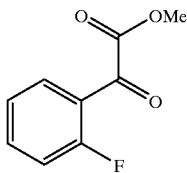

Methyl 2-fluorophenylglyoxylate was isolated as an oil in 94% yield. Carbon NMR (76 MHz, CDCl₃) δ 52.7, 116.4, 116.6, 121.7, 121.9, 123.8, 124.7, 130.8, 131.2, 132.0, 136.5, 136.6, 160.9, 164.3, 183.6.

EXAMPLE 4
General Synthesis Of Heteroarylglyoxylate Intermediates G & H

Oxalyl chloride (100 mmol) was added dropwise to a solution of a heterocyclyl glyoxylic acid (50 mmol) and DMF (1 mmol) in CH₂Cl₂ (25 mL). The resulting solution was stirred for 1 hour at room temperature after gas evolution ceased, then concentrated under vacuum to afford the acid chloride. This was dissolved in CH₂Cl₂ (25 mL) and added dropwise to an ice water cooled solution of methanol (5 mL, 125 mmol) and Et₃N (50 mmol) in CH₂Cl₂ (25 mL), then slowly warmed to room temperature and stirred overnight. The reaction was washed with aqueous HCl, followed with aqueous NaHCO₃, then dried (MgSO₄) and concentrated to afford intermediates G and H.

Intermediate G

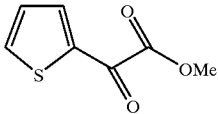

Methyl 2-thienylglyoxylate was isolated as a dark oil in 93% yield. Proton NMR (90 MHz, CDCl₃) δ 4.0 (s, 3H), 7.2 (t, 1H, J=5 Hz), 7.8 (d, 1H, J=5 Hz), 8.0 (d, 1H, J=5 Hz). Carbon NMR (76 MHz, CDCl₃) δ 52.6, 128.4, 136.8, 137.1, 138.9, 161.8, 175.8. GC/MS m/e=170.

Intermediate H

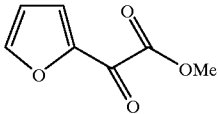

Methyl 2-furanylglyoxylate was isolated as a dark solid in 65% yield. Proton NMR (90 MHz, CDCl₃) δ 4.0 (s, 3H), 6.6 (m, 1H), 7.8 (m, 2H). Carbon NMR (76 MHz, CDCl₃) δ 52.8, 112.8, 124.3, 149.4, 149.8, 161.5, 170.8. GC/MS m/e=154.

EXAMPLE 5
General Synthesis Of Oxime Ester Intermediates I–O

O-tert-butylhydroxylamine hydrochloride (1 equivalent) was added to a solution of 8–14 mmol of methyl phenylglyoxylate or one of intermediates D–H dissolved in a mixture of pyridine (10 mL) and MeOH (10 mL). The reaction was stirred at room temperature overnight and confirmed by GC-MS to be complete, then concentrated under vacuum to remove most of the pyridine and MeOH. The concentrated material was diluted with CHCl₃ and extracted with dilute aqueous HCl, followed by saturated aqueous NaHCO₃. The organic solution was dried (MgSO₄) and concentrated to give an E/Z mixture of oxime isomers of intermediates I–O.

Intermediate I

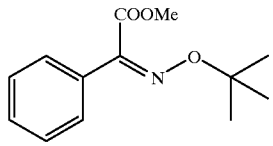

Intermediate J

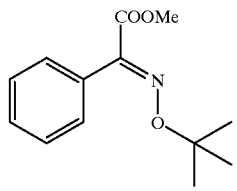

Methyl phenylglyoxylate O-tert-butyloxime was separated into pure Z and E isomers by silica chromatography eluted with a step gradient from 3:7 CHCl₃/hexane to 1:1 CHCl₃/hexane. Intermediate I eluted first as a light yellow oil in 36% yield. Proton NMR (90 MHz, CDCl₃), δ 1.2 (s, 9H), 3.8 (s, 3H), 7.3–7.5 (m, 5H). IR (thin film) 1745 cm⁻¹ Intermediate J eluted last as a light yellow oil in 26% yield. Proton NMR (90 MHz, CDCl₃), δ 1.3 (s, 9H) 3.8 (s, 3H), 7.3–7.33 (m, 5H). IR (thin film) 1727 cm⁻¹.

Intermediate K

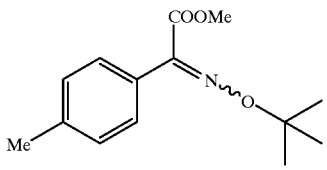

Methyl 4-methylphenylglyoxylate O-tert-butyloxime was purified by kugelrohr distillation to remove the methyl 4-methylbenzoate impurity, leaving a pot residue of an E/Z mixture of oximes. Proton NMR (90 MHz, CDCl₃), δ 1.4 (s, 3H), 2.38 and 2.4 (s, 3H, E and Z isomers), 3.85 and 3.9 (s, 3H, E and Z isomers), 7.1–8.1 (s, 4H). GC/MS (major and minor isomer m/e=249).

Intermediate L

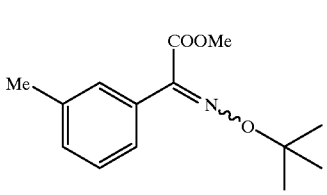

Methyl 3-methylphenylglyoxylate O-tert-butyloxime was isolated in quantitative yield as a mixture of 68% Z isomer and 26% E isomer plus a small amount of methyl 3-methylbenzoate. Proton NMR (90 MHz, CDCl₃), δ 1.3 (s, 9H), 2.4, (s, 3H), 3.85 and 3.89 (s, 3H, E and Z isomers) 7.0–7.4 (m, 4H). Carbon NMR (76 MHz, CDCl₃) δ 21.3, 21.2, 27.5, 51.8 (Z isomer), 52.3 (E isomer), 80.1 (Z), 81.4 (E), 123.3, 126.6, 126.8, 128.3, 128.5, 129.9, 130.1, 130.7, 131.2, 137.3, 138.3, 147.8, 149.8, 164.7, 164.8. GC/MS m/e of 249 for each isomer.

Intermediate M

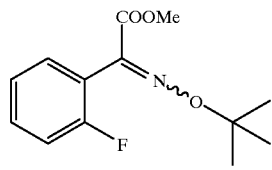

Methyl 2-fluorophenylglyoxylate O-tert-butyloxime was isolated in 69% yield as a 2:1 mixture of E/Z oxime isomers contaminated with some methyl 3-fluorobenzoate. Proton NMR (90 MHz, CDCl$_3$), δ 1.3 and 1.4 (s, 9H, E and Z isomers), 3.8 and 3.82, (s, 3H, E and Z isomers), 6.9–7.5 (m, 4H). IR(thin film) 1728 cm$^{-1}$. GC/MS m/e=253 for the two isomers.

Intermediate N

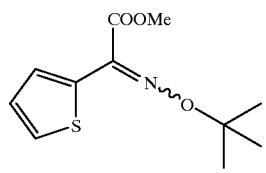

Methyl 2-thienylglyoxylate O-tert-butyloxime was isolated as an oil in 79% yield as a mixture of E/Z oxime isomers. Proton NMR (90 MHz, CDCl$_3$) δ 1.3 and 1.4 (s,9H, E and Z isomers), 4.0 (s, 3H), 7.2 (t, 1H, J=5 Hz), 6.9–7.8 (m, 3H). GC/MS m/e=241 for both the E and Z isomer peaks.

Intermediate O

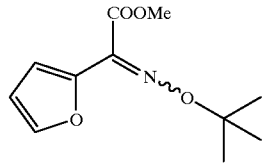

Methyl 2-furanylglyoxylate O-tert-butyloxime was isolated in 86% yield as a mixture of E/Z oxime isomers. Proton NMR (90 MHz, CDCl$_3$) δ 1.3 and 1.4 (s, 9H, E and Z isomers), 3.9 (s, 3H), 6.4–7.4 (m, 3H). GC/MS m/e=225.

EXAMPLE 6

General Synthesis Of Oxime Ester Intermediates P–S

A solution of an O-(tert-alkyl)hydroxylamine free base (7 mmol) and 6 equivalents of Et$_3$N in anhydrous hexane (32 mL) was sparged with nitrogen for 10 minutes, then cooled with an ice water bath while a solution of TiCl$_4$ (0.66 mL, 6.0 mmol) in hexane (16 mL) was slowly added dropwise. After the mixture was homogenized by vigorous stirring, a solution of methyl phenylglyoxylate (1.2 g, 7.3 mmol) in 1:1 ether/hexane (16 mL) was added in a single portion. The ice water cooling bath was removed and the reaction refluxed at 55° C. for 8 hours, then diluted with Et$_2$O (20 mL), filtered, and concentrated to give an E/Z mixture of intermediates P–S.

Intermediate P

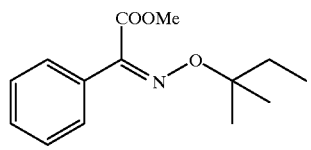

Intermediate Q

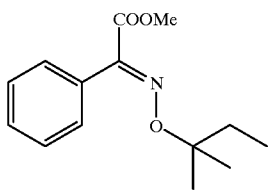

Methyl phenylglyoxylate O-tert-amyloxime was separated into pure Z and E isomers by silica chromatography eluted with a 1:1 CHCl$_3$/hexane. Intermediate P eluted first as an oil in 21% yield. Proton NMR (90 MHz, CDCl$_3$), δ 0.8 (t, 3H, J=7 Hz), 1.2 (s, 6H), 1.6 (q, 2H), 3.9 (s, 3H), 7.2–7.6 (m, 5H). Intermediate Q eluted last as an oil in 29% yield. Proton NMR (90 MHz, CDCl$_3$), δ 0.8 (t, 3H, J=7 Hz), 1.3 (s, 6H), 1.7 (q, 2H), 3.8 (s, 3H), 7.2–7.5 (m, 5H).

Intermediate R

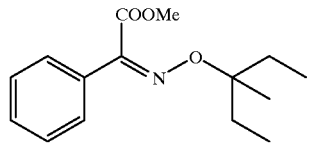

Intermediate S

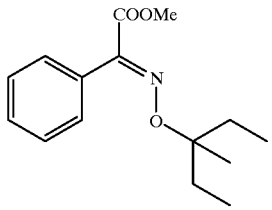

Methyl phenylglyoxylate O-(3-methyl-3-pentyl)oxime was separated into pure Z and E isomers by silica chromatography eluted with 7:3 CHCl$_3$/hexane. Intermediate R eluted first as an oil in 9% yield. Proton NMR (90 MHz, CDCl$_3$), δ 0.8 (t, 6H, J=7 Hz), 1.2 (s, 3H), 1.6 (m, 4H), 3.9 (s, 3H), 7.2–7.6 (m, 5H). Intermediate S eluted last as an oil in 27% yield. Proton NMR (90 MHz, CDCl$_3$), δ 0.8 (t, 6H, J=7 Hz), 1.2 (s, 3H), 1.6 (t, 4H), 3.8 (s, 3H), 7.2–7.5 (s, 5H).

EXAMPLE 7

Synthesis Of Hydrazone Ester Intermediates T & U

A solution of methyl phenylglyoxylate (3.60 g, 22 mmol) and tert-butylhydrazine hydrochloride (2.70 g, 22 mmol) in a mixture of pyridine (10 mL) and methanol (10 mL) was stirred at room temperature overnight. The incomplete reaction was refluxed and monitored to completion over 3 hours by GC and TLC eluted with 2:3 CHCl$_3$/hexane, then concentrated under vacuum and the residue redissolved in CHCl$_3$. After washing with saturated aqueous NaHCO$_3$, the CHCl$_3$ solution was dried (MgSO$_4$) and concentrated to give 4.2 g of a mixture of E/Z-O-methyl phenylglyoxylate N-(tert-butyl)hydrazones which separated into pure Z and E isomers by silica chromatography eluted with a step gradient of 100% CHCl$_3$ to 97.5:2.5 CHCl$_3$/Et$_2$O.

Intermediate T

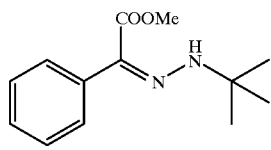

Intermediate U

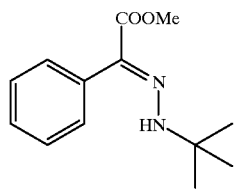

Intermediate T eluted first to give 2.8 g of a light yellow oil in 54% yield. Proton NMR (90 MHz, CDCl$_3$), δ 1.3 (s, 9H), 3.8 (s, 3H), 7.1–7.7 (m, 5H). IR (thin film) 1673 cm$^{-1}$. Intermediate U eluted last to give 0.6 g of a light yellow oil in 12% yield. Proton NMR (90 MHz, CDCl$_3$), δ 1.2 (s, 9H), 3.8 (s, 3H), 7.0–7.5 (m, 5H). IR (thin film) 1698 cm$^{-1}$.

EXAMPLE 8
General Synthesis Of Oxime Glyoxamide Samples 1–12

A solution of one of Intermediates I–S in at least 50 equivalents of propylamine was heated at 100–150° C. in a sealed tube, and monitored to completion by periodic sampling and GC-MS analysis. Reaction times ranged from a couple of hours up to 24 hours, and both E and Z isomers reacted with no isomerization of the oxime geometry. Concentration of the reaction under vacuum gave the N-propylamide derivative. Using this method, Samples 1–12 were prepared in excellent yield unless otherwise noted below.

Sample 1-N-Propyl Phenylglyoxamide, Z-[O-(tert-Butyl)oxime]

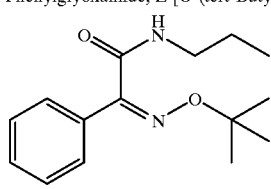

Isolated as a solid with mp 103–105° C. Proton NMR (90 MHz, CDCl$_3$), δ 1.0 (t, 3H, J=7 Hz), 1.4 (s, 9H), 1.4 (sextet, 2H, J=7 Hz), 3.4 (q, 2H, J=7 Hz), 6.1 (s, broad, 1H), 7.2–7.7 (m, 5H). GC/MS (M$^+$-$^t$Bu)=206.

Sample 2-N-Propyl Phenylglyoxamide, E-[O-(tert-Butyl)oxime]

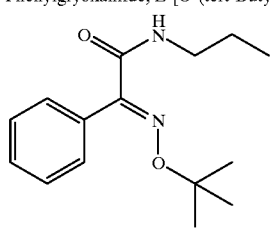

Isolated as a solid with mp 53–55° C. Proton NMR (90 MHz, CDCl$_3$), δ 1.0 (t, 3H, J=7 Hz), 1.3 (s, 9H), 1.5 (sextet, 2H, J=7 Hz), 3.4 (q, 2H, J=7 Hz), 6.8 (s, broad, 1H), 7.2–7.7 (m, 5H). GC/MS (M$^+$-$^t$Bu)=206.

Sample 3-N-Propyl Phenylglyoxamide, Z-[O-(tert-Amyl)oxime]

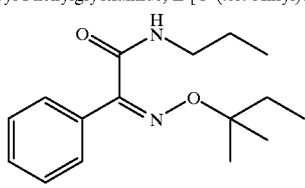

Isoated as a light yellow oily solid. Proton NMR (90 MHz, CDCl$_3$), δ 0.8 (t, 3H, J=7 Hz), 0.82 (t, 3H, J=7 Hz), 1.2 (s, 6H), 1.2–1.7 (m, 4H), 3.3 (q, 2H, J=7 Hz), 6.1 (s, 1H, broad, NH, Z isomer), 7.2–7.7 (m, 5H).

Sample 4-N-Propyl Phenylglyoxamide, E-[O-(tert-Amyl)oxime]

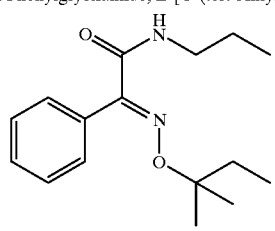

Isolated as a light yellow oily solid. Proton NMR (90 MHz, CDCl$_3$), δ 0.8 (t, 3H, J=7 Hz), 0.9 (t, 3H, J=7 Hz), 1.2 (s, 6H), 1.4–1.8 (m, 4H), 3.3 (q, 2H, J=7 Hz), 6.8 (s, 1H, broad, NH, E isomer), 7.2–7.6 (m, 5H).

Sample 5-N-Propyl Phenylglyoxamide, Z-[O-(3-Methyl-3-pentyl)oxime]

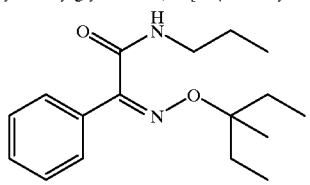

Isolated as dark amber oil. Proton NMR (90 MHz, CDCl$_3$), δ 0.8 (t, 6H, J=7 Hz), 0.9 (t, 3H, J=7 Hz), 1.2 (s, 3H), 1.3–1.8 (m, 6H), 3.3 (q, 2H, J=7 Hz), 6.1 (s, 1H broad NH peak, Z isomer), 7.2–7.8 (m, 5H).

Sample 6-N-Propyl Phenylglyoxamide, E-[O-(3-Methyl-3-pentyl)oxime]

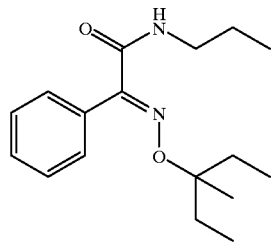

Isolated as pale oil. Proton NMR (90 MHz, CDCl$_3$), δ 0.8 (t, 6H, J=7 Hz), 0.9 (t, 3H, J=7 Hz), 1.2 (s, 3H), 1.3–1.8 (m, 6H), 3.3 (q, 2H, J=7 Hz), 6.8 (s, 1H, broad NH peak, E isomer), 7.2–7.6 (m, 5H).

Sample 7-N-Propyl 4-Methylphenylglyoxamide, E/Z-[O-(tert-Butyl)oxime]

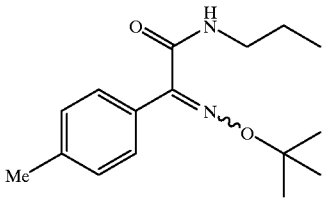

Crude material was chromatographed on silica, eluted with a step gradient from CHCl$_3$ to 9:1 CHCl$_3$/Et$_2$O, to give 333 mg of a yellow waxy solid in 29% yield. Proton NMR (90 MHz, CDCl$_3$), δ 1.0 (t, 3H, J=7 Hz), 1.4 (s, 9H), 1.6 (septet, 2H, J=7 Hz), 2.3 (s, 3H), 3.2–3.5 (m, 2H), 6.0 and 6.8 (s, 1H, broad, NH of E and Z isomers), 7.1–7.6 (m, 4H). Carbon NMR (76 MHz, CDCl$_3$) δ 11.1, 11.2, 21.1, 21.2, 22.6, 22.7, 27.3, 40.8, 41.0, 80.1, 80.4, 126.4, 126.6, 128.0, 128.7, 128.9, 129.1, 130.0, 138.9, 139.3, 149.1, 151.5, 163.3, 163.6.

Sample 8-N-Propyl 3-Methylphenylglyoxamide, E/Z-[O-(tert-Butyl)oxime]

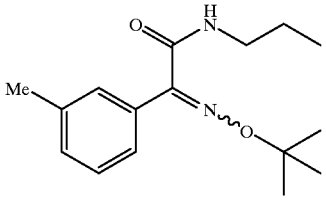

Crude material was chromatographed on silica, eluted with a step gradient from CHCl$_3$ to 9:1 CHCl$_3$/Et$_2$O, to give 338 mg of a yellow oil in 29% yield. Proton NMR (90 MHz, CDCl$_3$), δ 0.9 (t, 3H, J=7 Hz), 1.3 (s, 9H), 1.6 (sextet, 2H, J=7 Hz), 2.3 (s, 3H), 3.3 (pentet, 2H), 6.2 and 6.8 (s, 1H, broad, NH of E and Z isomers), 7.0–7.5 (m, 4H). Carbon NMR (76 MHz, CDCl$_3$) δ 11.1, 11.2, 21.2, 21.2, 22.7, 22.8, 27.4, 40.9, 41.1, 80.3, 80.5, 123.9, 126.9, 127.2, 127.3, 128.1, 129.7, 130.1, 130.3, 136.8, 137.7, 151.5, 163.3, 163.6.

Sample 9-N-Propyl 2-Fluorophenylglyoxamide, E/Z-[O-tert-Butyl)oxime]

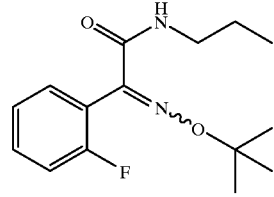

Crude material was chromatographed on silica, eluted with 5% ether in chloroform to give 326 mg of a yellow oil in 29% yield. Proton NMR (90 MHz, CDCl$_3$), δ 0.9 (t, 3H, J=7 Hz), 1.3 and 1.37 (s, 9H, E and Z isomers), 1.55 (sextet, 2H, J=7 Hz), 3.3 (m, 2H), 6.5–7.5 (m, 4H).

Sample 10-N-Propyl 2-Thienylglyoxylate, E-[O-(tert-Butyl)oxime]

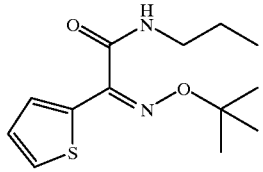

Crude material was chromatographed on silica eluted with 9:1 hexane/EtOAc to give 700 mg of a light yellow oil in 65% yield. Proton NMR (90 MHz, CDCl$_3$) δ 1.0 (t, 3H, J=7 Hz), 1.4 (s, 9H), 1.5 (septet, 2H, J=7 Hz), 3.3 (q, 2H, J=7 Hz), 6.8 (s, 1H, broad), 7.1 (t, 1H, J=5 Hz), 7.5 (d, 1H, J=5 Hz), 8.3 (d, 1H, J=5 Hz). Carbon NMR (76 MHz, CDCl$_3$) δ 11.1, 22.7, 27.6, 41.2, 82.0, 125.9, 128.8, 130.2, 133.0, 143.0, 163.5. GC/MS m/e=268.

Sample 11-N-Propyl 2-Thienylglyoxylate, Z-[O-(tert-Butyl)oxime]

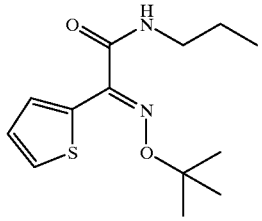

The crude material which afforded Sample 10 was further eluted with 9:1 hexane/EtOAc to give 200 mg of this isomer as an ivory colored solid in 18% yield. Proton NMR (90 MHz, CDCl$_3$) δ 1.0 (t, 3H, J=7 Hz), 1.3 (s, 9H), 1.5 (septet, 2H, J=7 Hz), 3.3 (q, 2H, J=7 Hz), 6.6 (s, 1H, broad), 6.9 (t, 1H, J=5 Hz), 7.2 (d, 1H, J=5 Hz), 7.4 (d, 1H, J=5 Hz). Carbon NMR (76 MHz, CDCl$_3$) δ 11.3, 22.6, 27.4, 41.1, 81.4, 127, 127.4, 128.4, 136.5, 146.5, 161.4. GC/MS m/e=268.

Sample 12-N-Propyl 2-Furanylglyoxylate, E/Z-[O-(tert-Butyl)oxime]

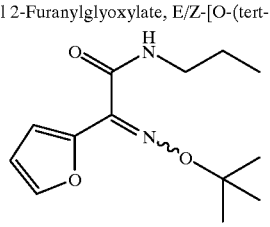

The crude material was chromatographed on silica eluted with 4:2 hexane/EtOAc to give 800 mg of an oil in 71% yield. Proton NMR (90 MHz, CDCl$_3$) δ 0.8 (t, 3H, J=7 Hz), 1.2 and 1.25 (s, 9H, E and Z isomers), 1.5 (septet, 2H, J=7 Hz), 3.2 (q, 2H, J=7 Hz), 6.4–7.4 (m, 4H). Carbon NMR (76 MHz, CDCl$_3$) δ 11.0, 11.1, 22.4, 22.5, 27.1, 27.3, 40.9, 41.0, 80.9, 81.0, 110.9, 111.1, 112.5, 118.4, 127, 140.5, 143.1, 143.5, 147.3, 160.8, 162.4. GC/MS m/e=252 for each of two closely eluting peaks.

EXAMPLE 9

Sample 13—N-Allyl phenylglyoxamide, E/Z-[O-(tert-Butyl)oxime]

A solution of N-allyl phenylglyoxamide (3.50 g, 18 mmol) and O-(tert-butyl)hydroxylamine hydrochloride (2.55 g, 20 mmol) in a mixture of pyridine (20 mL) and ethanol (20 mL) was refluxed and monitored to completion over 3 hours by GC and TLC eluted with CHCl₃. This solution was concentrated under vacuum, then the residue was redissolved in CHCl₃ and washed with dilute aqueous HCl, followed with saturated aqueous NaHCO₃. The organic solution was dried (MgSO₄) and concentrated to 3.2 g of a pale yellow solid, which was slurried in 25 mL of 5% EtOAc in hexane and filtered to give 1.8 g of Sample 13 as a cream colored solid in 38% yield. mp 91–92° C. Proton NMR (90 MHz, CDCl₃), δ 1.4 (s, 9H), 3.8–6.0 (m, ABX2, 4H), 6.2 (s, broad, 1H), 7.2–7.7 (m, 5H).

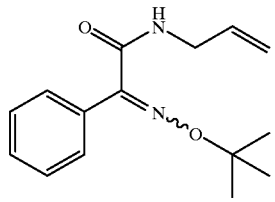

EXAMPLE 10
Sample 14—N-Allyl phenylglyoxamide, E/Z-[N-(tert-Butyl)hydrazone]

A solution of N-allyl phenylglyoxamide (3.50 g, 18 mmol) and O-(tert-butyl)hydroxylamine hydrochloride (2.55 g, 20 mmol) in a mixture of pyridine (20 mL) and ethanol (20 mL) was refluxed and monitored to completion over 3 hours by GC and TLC eluted with CHCl₃. This solution was concentrated under vacuum, then the residue was redissolved in CHCl₃ and washed with saturated aqueous NaHCO₃. The organic solution was dried (MgSO₄) and concentrated to 4.56 g of an amber oil. Purification was effected by silica chromatography eluted with CHCl₃ to give 1.1 g of Sample 14 as a yellow oil in 24% yield. Proton NMR (90 MHz, CDCl₃), δ 1.3 (s, 9H), 3.8–6.0 (ABX2, 4H), 7.3–7.4 (m, 5H), 10.5 (s, broad, 1H). GC/MS m/e=259.

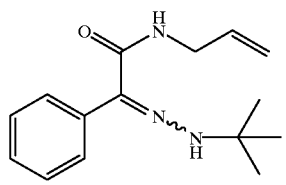

BIOLOGICAL ASSAYS

The compounds prepared in the above Examples have demonstrated control of Ggt in one or both of the following test methods. The results are shown in the table below.

In Vitro Assay

The test compounds (0.25 mL of an appropriate stock solution in acetone) were incorporated into 25 mL minimal media agar [prepared by autoclaving a solution of 17.5 g Czapek Dox broth (Difco), 7.5 g purified agar or Bacto-agar (Difco), and 500 mL distilled/deionized water, and then adding 50 μL of 1 mg/mL thiamine hydrochloride and 50 μL of 1 mg/mL biotin in 5% ethanol] and plates were prepared.

Each plate was inoculated by placing in a triangular shape three 4 mm plugs of Ggt grown on the minimal media agar described above. The plates were incubated in the dark at 19–20° C. for 4–5 days. The growth of the fungus was measured as the diameter of the mycelial growth and the result expressed as Percent Inhibition, calculated as [1-[(mm growth on treated plate—4)/(mm growth on control plate—4)]]×100.

4 Week In Vivo Seed Treatment Assay

The test compounds were tested for control of Ggt on "Bergen" varieties of wheat grown in 3 inch square pots containing soil (equal to thirds of Metro-mix, sand, and silt-loam filed soil, all steam sterilized). Seeds were treated with a solution of a test compound in acetone. Using a 10,000 ppm stock for each compound, the following serial dilutions were prepared.

| Solution Number | Concentration (ppm) | (gm of ai)/(100 kg/seed) when 1 mL applied to 10 gm seed |
|---|---|---|
| 1 | 10,000 | 100 |
| 2 | 2,500 | 25 |

When 1 mL of the stock and dilutions was applied to 10 gm of seed, the resultant application rates were 100 and 25 g of active ingredient per 100 kg of seed.

A treatment jar was rinsed 2 times with 3 mL of acetone. The 1 mL of the solution was swirled to cover the base of the jar. 10 gm of seed was added to the jar and capped, after which the jar was swirled and shaken until the seeds got a rapid and even coverage. After about 30–50 seconds, the lid was removed while the shaking was continued. After 1 minute, the jar was set aside to dry. When dry, the seed was poured into an envelope for storage until planting.

Compounds were tested for control of Ggt on "Bergen" varieties of wheat grown in 3 inch square pots containing soil infested with Ggt. The infestation was accomplished by mixing the soil with an inoculum prepared by growing Ggt on infested sterile oats (400 cc whole oats, 350 mL deionized water, autoclaved). After a one month incubation period at room temperature, the oats were dried and mixed with the soil at 4% v/v.

The roots were harvested, washed, and rated after 4 weeks. Each treatment was assigned a percent (%) diseased root area value using 1, 5, 10, 20, 30, 40, 50, 60, 80, or 100% ratings. Each pot of plants got a single rating.

Results

The following table reports the results of in-vitro tests carried out with examples of compounds of the invention produced by the methods generally described above. They are compared with a compound disclosed in previous patents which is very effective against Ggt. For that reference compound and two of the compounds of the invention, the results of in-vivo tests are reported.

The results of the in vitro assay and the 4 week in vivo seed treatment assay are shown in the table below.

| Example No. | Structure | Geometry | % Control of Ggt In Vitro | | | | % Control of Ggt In Vivo | |
|---|---|---|---|---|---|---|---|---|
| | | | 10 ppm | 1 ppm | 0.1 ppm | 0.01 ppm | 100 g al/ 100 kg seed | 25 g al/ 100 kg seed |
| Standard | 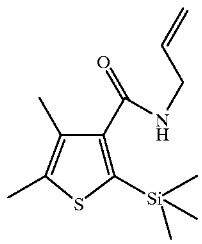 | | 100 | 100 | 100 | 100 | 93 | 90 |
| 1 | 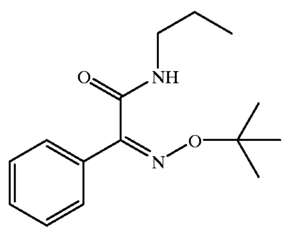 | Z | 100 | 100 | 96 | 4 | 79 | 71 |
| 2 | 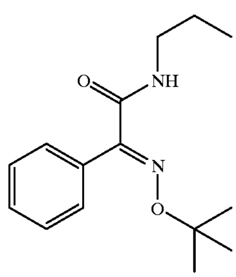 | E | 0 | 0 | 27 | | | |
| 3 | 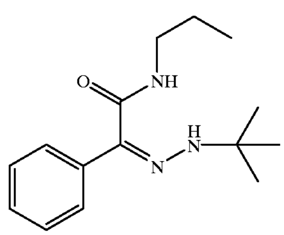 | Z | 97 | 89 | 19 | | 0 | 21 |
| 4 | 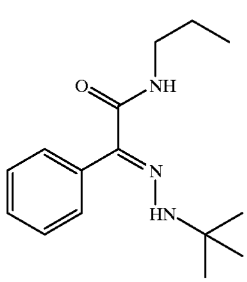 | E | 43 | 0 | 0 | | | |

-continued

| Example No. | Structure | Geometry | % Control of Ggt In Vitro | | | | % Control of Ggt In Vivo | |
|---|---|---|---|---|---|---|---|---|
| | | | 10 ppm | 1 ppm | 0.1 ppm | 0.01 ppm | 100 g al/ 100 kg seed | 25 g al/ 100 kg seed |
| 5 | 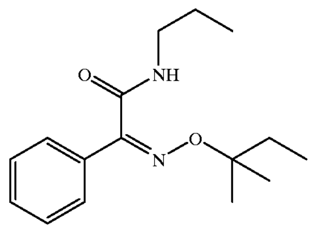 | Z | 100 | 100 | 100 | 59 | | |
| 6 | 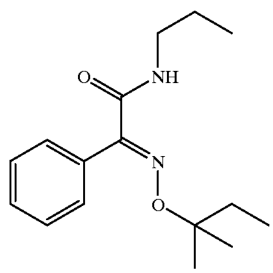 | E | 20 | 2 | 2 | | | |
| 7 | 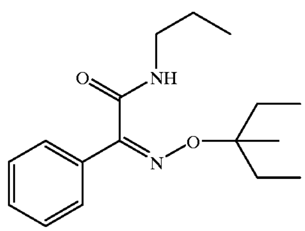 | Z | 100 | 100 | 98 | 16 | | |
| 8 | 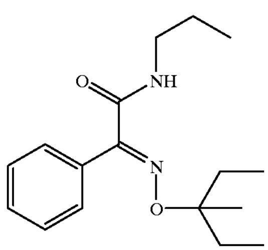 | E | 98 | 80 | 2 | | | |
| 9 | 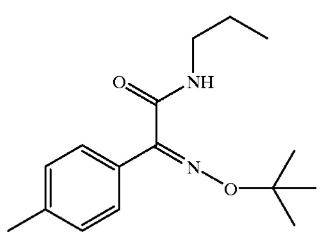 | E/Z | 80 | 37 | 7 | | | |

-continued
| Example No. | Structure | Geometry | % Control of Ggt In Vitro | | | | % Control of Ggt In Vivo | |
|---|---|---|---|---|---|---|---|---|
| | | | 10 ppm | 1 ppm | 0.1 ppm | 0.01 ppm | 100 g al/ 100 kg seed | 25 g al/ 100 kg seed |
| 10 | 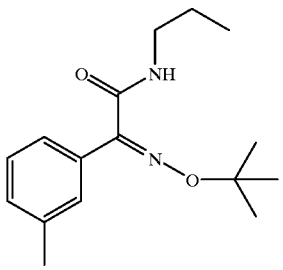 | E/Z | 80 | 32 | 5 | | | |
| 11 | 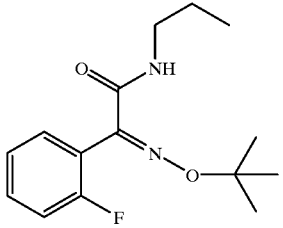 | E/Z | 77 | 43 | 0 | | | |
| 12 | 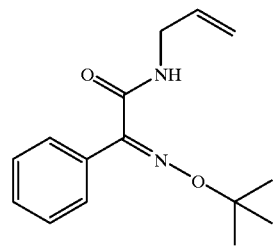 | E/Z | 100 | 98 | 67 | | | |
| 13 | 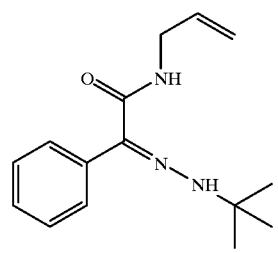 | E/Z | 96 | 96 | 25 | | | |
| 14 | 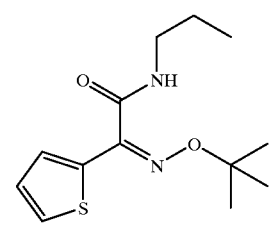 | E | 100 | 100 | 96 | | | |

-continued

| Example No. | Structure | Geometry | % Control of Ggt In Vitro | | | | % Control of Ggt In Vivo | |
|---|---|---|---|---|---|---|---|---|
| | | | 10 ppm | 1 ppm | 0.1 ppm | 0.01 ppm | 100 g al/ 100 kg seed | 25 g al/ 100 kg seed |
| 15 | 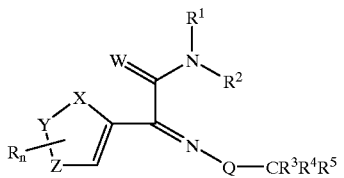 | Z | 94 | 20 | 10 | | | |
| 16 | 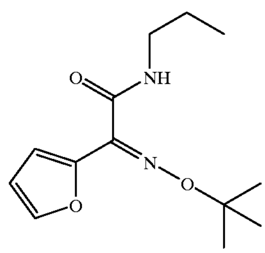 | E/Z | 92 | 51 | 24 | | | |

What is claimed is:

1. A compound having the following structural formula where

X and Y are each CH when Z is S, and the structural formula has a double bond between X and Y; or X is S when Y and Z are CH, and the structural formula has a double bond between Y and Z;

W is O or S;

Q is O, NH, or NMe;

n=0–2;

R is independently selected from halo or alkyl;

$R^1$ is selected from the group consisting of $C_1$–$C_{10}$ straight or branched alkyl, alkenyl, or alkynyl groups, each optionally substituted with one or more halogen, alkoxy, alkylthio; alkoxy, alkenoxy, alkynoxy, dialkylamino, or alkylthio;

$R^2$ is selected from the group consisting of hydrogen; $C_1$–$C_6$ straight or branched alkyl, alkenyl, or alkynyl groups, each optionally substituted with one or more halogen;

$R^3$, $R^4$ and $R^5$ are independently selected from the group consisting of alkyl, alkenyl, alkynyl, cycloalkyl, cycloalkenyl, and phenyl, each optionally substituted with halogen, alkoxy, or alkylthio;

and two of said $R^3$, $R^4$ and $R^5$ groups optionally combined to form a cyclo group which is cyclopropyl, cyclobutyl, cyclopentyl, or cyclohexyl.

2. A compound of claim 1, wherein X is S.

3. A compound of claim 2, wherein W is O, $R^1$ is propyl, and $R^2$ is hydrogen.

4. A compound of claim 2, wherein Q is O.

5. A compound of claim 4, where each of $R^3$, $R^4$ and $R^5$ is methyl.

6. A compound of claim 1, wherein said compound is a mixture of E and Z geometric isomers.

7. A compound of claim 1, wherein said compound is an E geometric isomer.

8. A compound of claim 1, wherein said compound is a Z geometric isomer.

9. A composition useful in controlling Take-All disease in a plant comprising applying to the plant locus a fungicidally effective amount of a compound of claim 1 and an adjuvant.

* * * * *